United States Patent
Mason et al.

(10) Patent No.: US 7,060,045 B2
(45) Date of Patent: *Jun. 13, 2006

(54) ORTHOSIS PROVIDING DYNAMIC TRACKING OF THE PATELLO-FEMORAL JOINT

(75) Inventors: Jeffrey T. Mason, Escondido, CA (US); James M. Fout, Oceanside, CA (US)

(73) Assignee: Breg, Inc., Vista, CA (US)

( * ) Notice: Subject to any disclaimer, the term of this patent is extended or adjusted under 35 U.S.C. 154(b) by 423 days.

This patent is subject to a terminal disclaimer.

(21) Appl. No.: 10/420,344

(22) Filed: Apr. 22, 2003

(65) Prior Publication Data

US 2004/0054307 A1   Mar. 18, 2004

Related U.S. Application Data

(63) Continuation-in-part of application No. 09/669,061, filed on Sep. 22, 2000, now Pat. No. 6,551,264.

(51) Int. Cl.
*A61F 5/00* (2006.01)

(52) U.S. Cl. .......................................... 602/5; 128/882

(58) Field of Classification Search ............ 602/5, 602/16, 23, 26, 60–63; 128/882
See application file for complete search history.

(56) References Cited

U.S. PATENT DOCUMENTS

| | | | |
|---|---|---|---|
| 3,581,741 A | 6/1971 | Rosman | 128/80 |
| 4,201,203 A | 5/1980 | Applegate | 128/80 |
| 4,296,744 A | 10/1981 | Palumbo | 128/80 |
| 4,370,978 A | 2/1983 | Palumbo | 128/80 |
| 4,423,720 A | 1/1984 | Meier et al. | 128/80 |
| 4,425,912 A | 1/1984 | Harper | 128/80 |
| 4,445,505 A | 5/1984 | Labour et al. | 128/80 |
| 4,466,428 A | 8/1984 | McCoy | 128/80 |
| 4,506,661 A | 3/1985 | Foster | 128/80 |
| 4,554,913 A | 11/1985 | Womack et al. | 128/80 |
| 4,572,170 A | 2/1986 | Cronk et al. | 128/80 |
| 4,607,628 A | 8/1986 | Dashefsky | 128/80 |
| 4,633,867 A | 1/1987 | Kausek et al. | 128/80 |
| 4,681,097 A | 7/1987 | Pansiera | 128/77 |
| 4,854,308 A | 8/1989 | Drillo | 128/80 |
| 4,872,448 A | 10/1989 | Johnson, Jr. | 128/80 |
| 4,991,571 A | 2/1991 | Kausek | 128/80 C |
| 5,024,216 A | 6/1991 | Shiono | 128/80 |
| 5,277,697 A | 1/1994 | France et al. | 602/16 |
| 5,288,287 A | 2/1994 | Castillo et al. | 602/16 |
| 5,458,565 A | 10/1995 | Tillinghast, III et al. | 602/26 |
| 5,554,105 A | 9/1996 | Taylor | 602/26 |

(Continued)

*Primary Examiner*—Henry Bennett
(74) *Attorney, Agent, or Firm*—Rodney F. Brown

(57) ABSTRACT

A knee orthosis is provided having upper and lower arms and a hinge assembly positionable about the knee to one side of the patella. The hinge assembly has a hinge pivot and a tension strap lever. The upper and lower arms and tension strap lever are each rotatable about the hinge pivot. A compression member is positioned in engagement with the knee on the opposite side of the patella from the hinge assembly and a tension strap is connected to the compression member and the tension strap lever. The tension strap applies a tension force to the compression member which increases when the upper and lower arms and tension strap lever rotationally transition from a flexion position to an extension position and decreases when the upper and lower arms and tension strap lever rotationally transition from the extension position to the flexion position.

25 Claims, 7 Drawing Sheets

U.S. PATENT DOCUMENTS

| | | |
|---|---|---|
| 5,556,374 A | 9/1996 | Grace et al. .................. 602/26 |
| 5,613,943 A | 3/1997 | Palumbo ...................... 602/62 |
| 5,759,167 A * | 6/1998 | Shields et al. ................ 602/26 |
| 5,797,864 A | 8/1998 | Taylor ......................... 602/26 |
| 5,807,298 A | 9/1998 | Palumbo ...................... 602/62 |
| 5,857,988 A | 1/1999 | Shirley ........................ 602/26 |
| 5,865,776 A | 2/1999 | Springs ........................ 602/26 |
| 5,873,848 A | 2/1999 | Fulkerson ..................... 602/62 |
| RE37,297 E | 7/2001 | Smith, III ..................... 602/26 |
| 6,287,269 B1 * | 9/2001 | Osti et al. ..................... 602/62 |
| 6,290,664 B1 * | 9/2001 | Nauert ......................... 602/16 |
| 6,551,264 B1 * | 4/2003 | Cawley et al. ................ 602/16 |
| 6,592,538 B1 * | 7/2003 | Hotchkiss et al. ............ 602/26 |

* cited by examiner

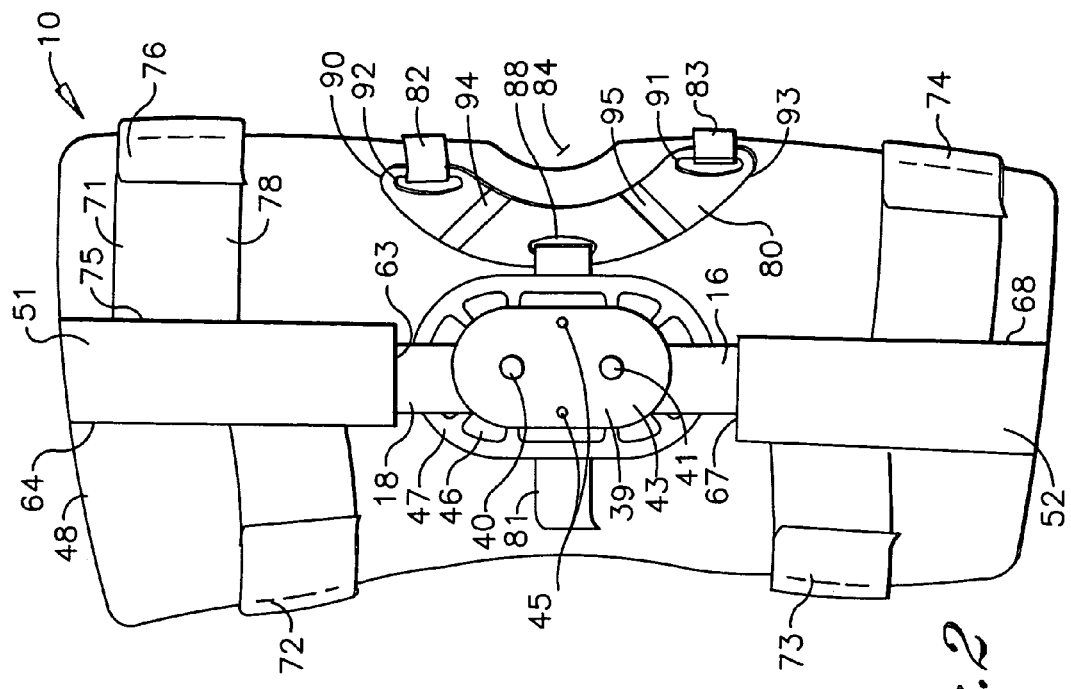
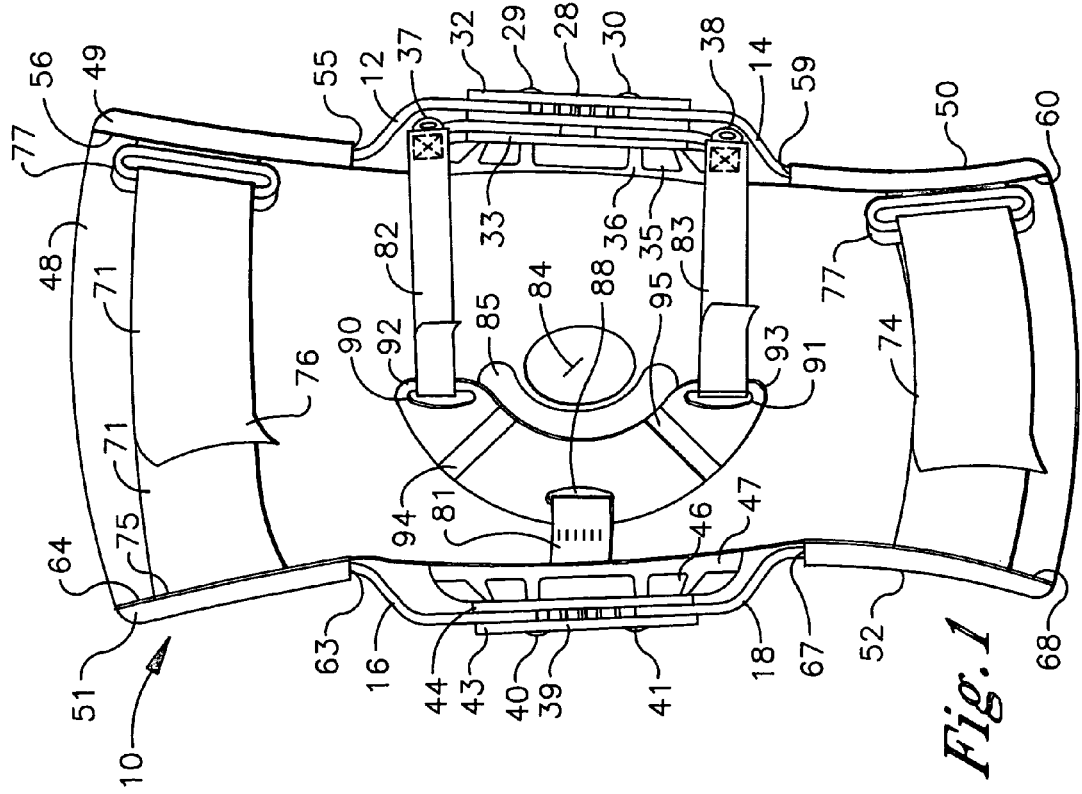

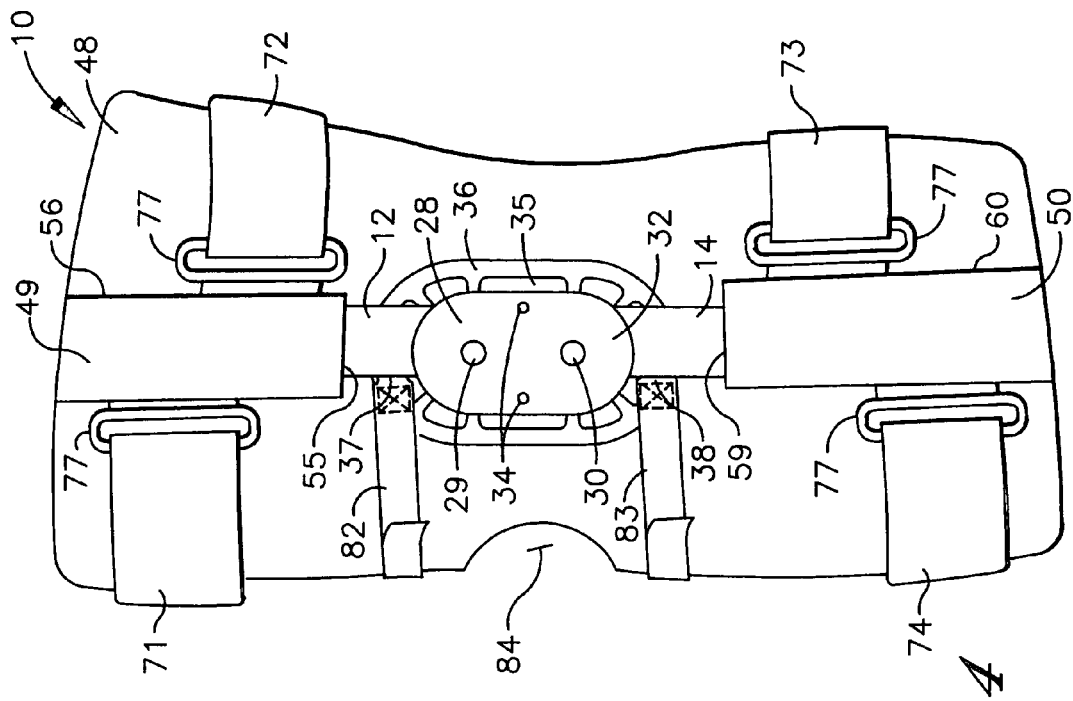
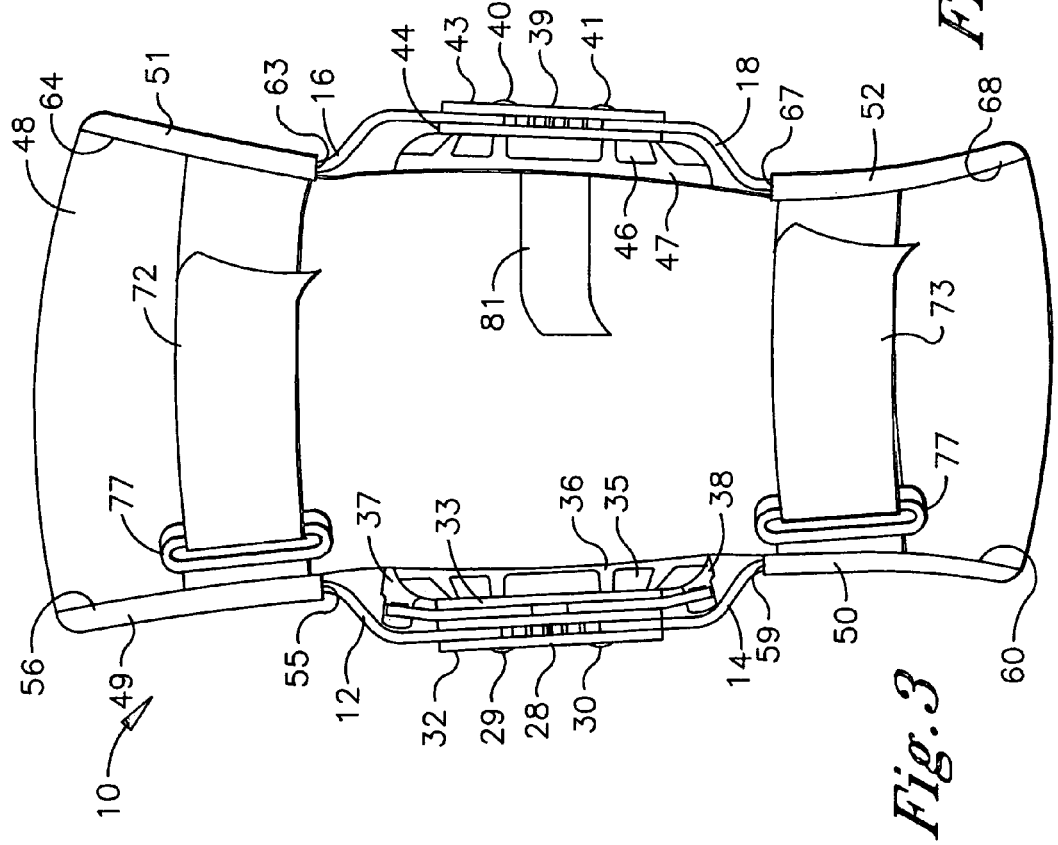
Fig. 3
Fig. 4

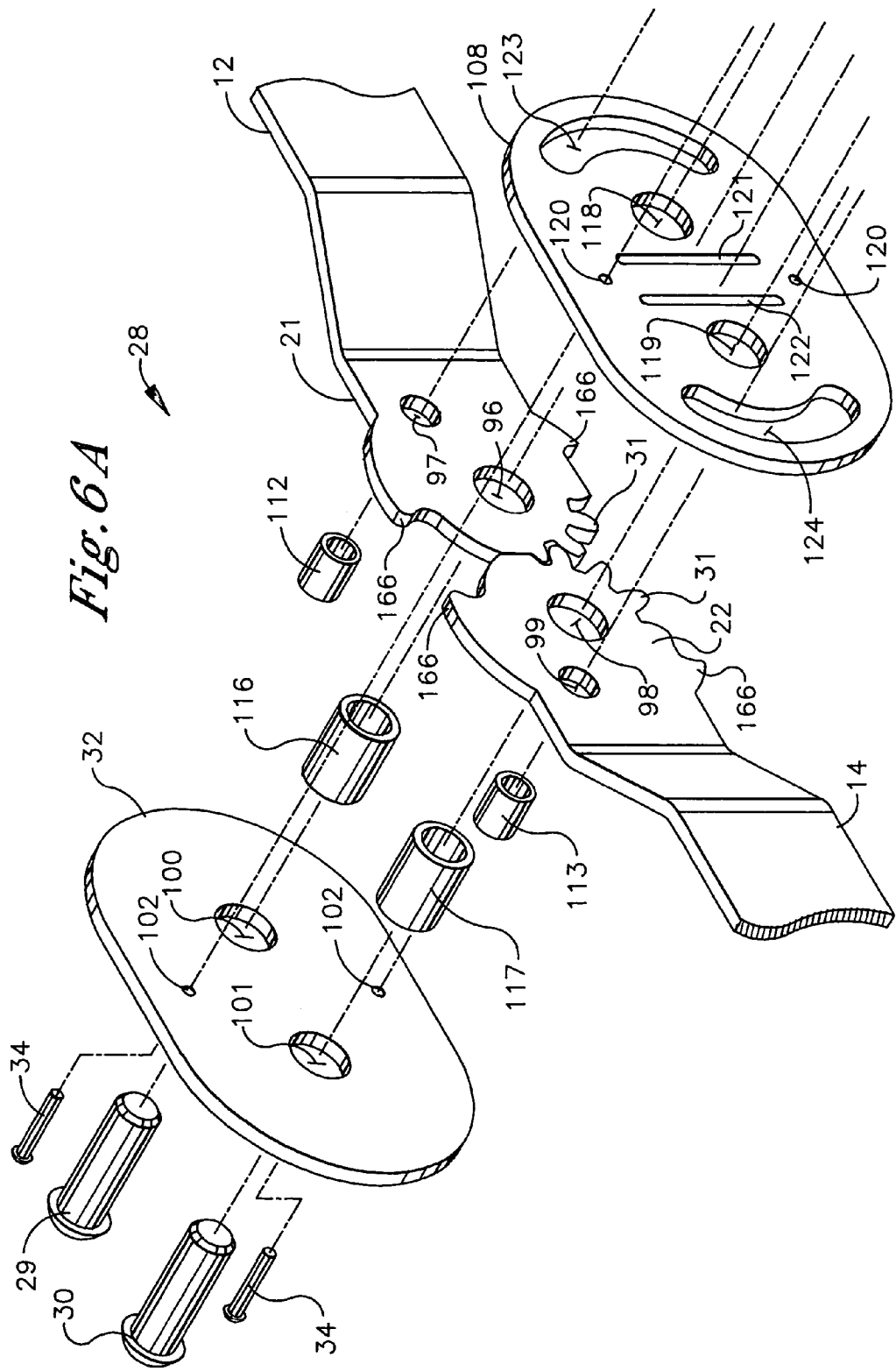

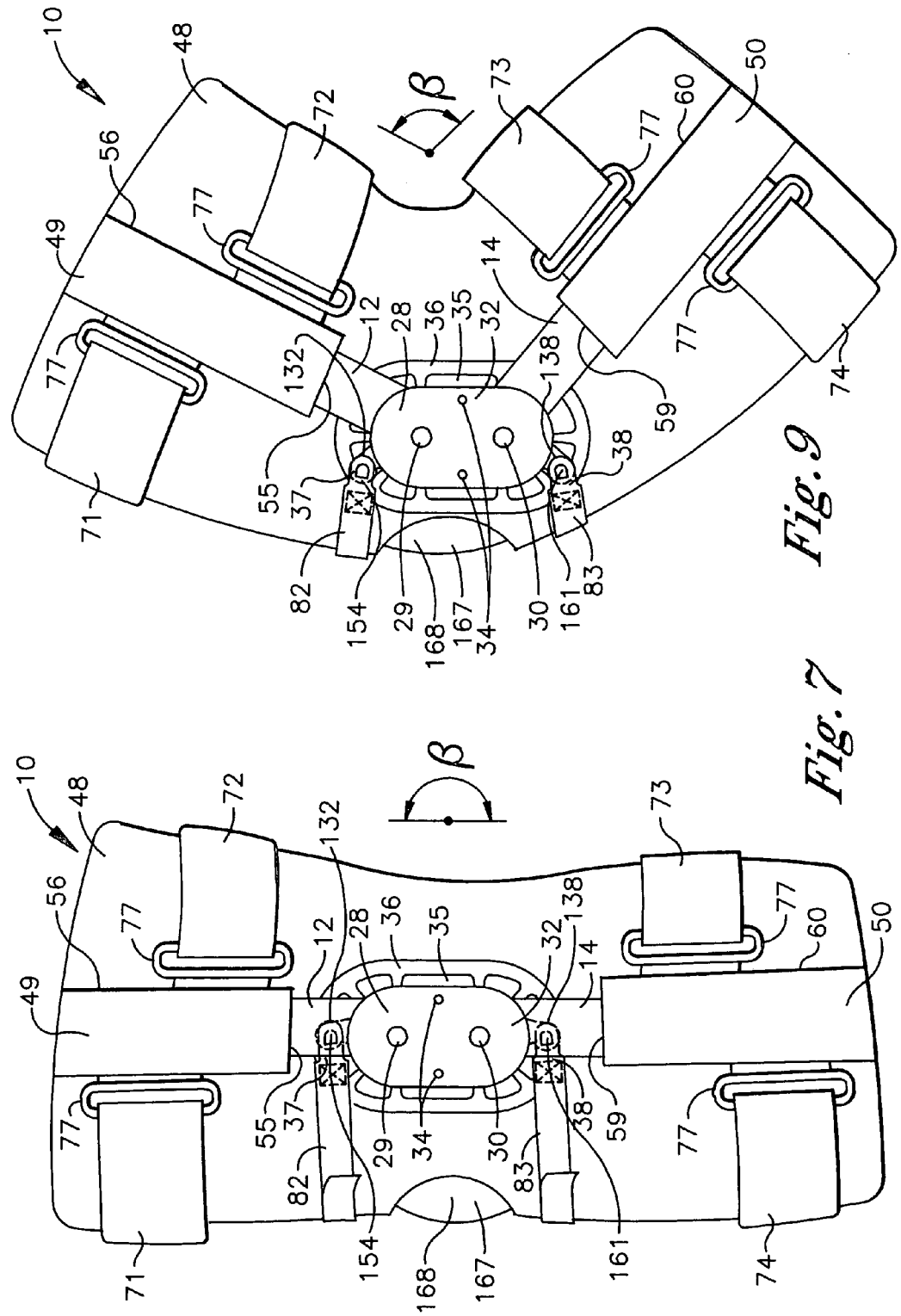

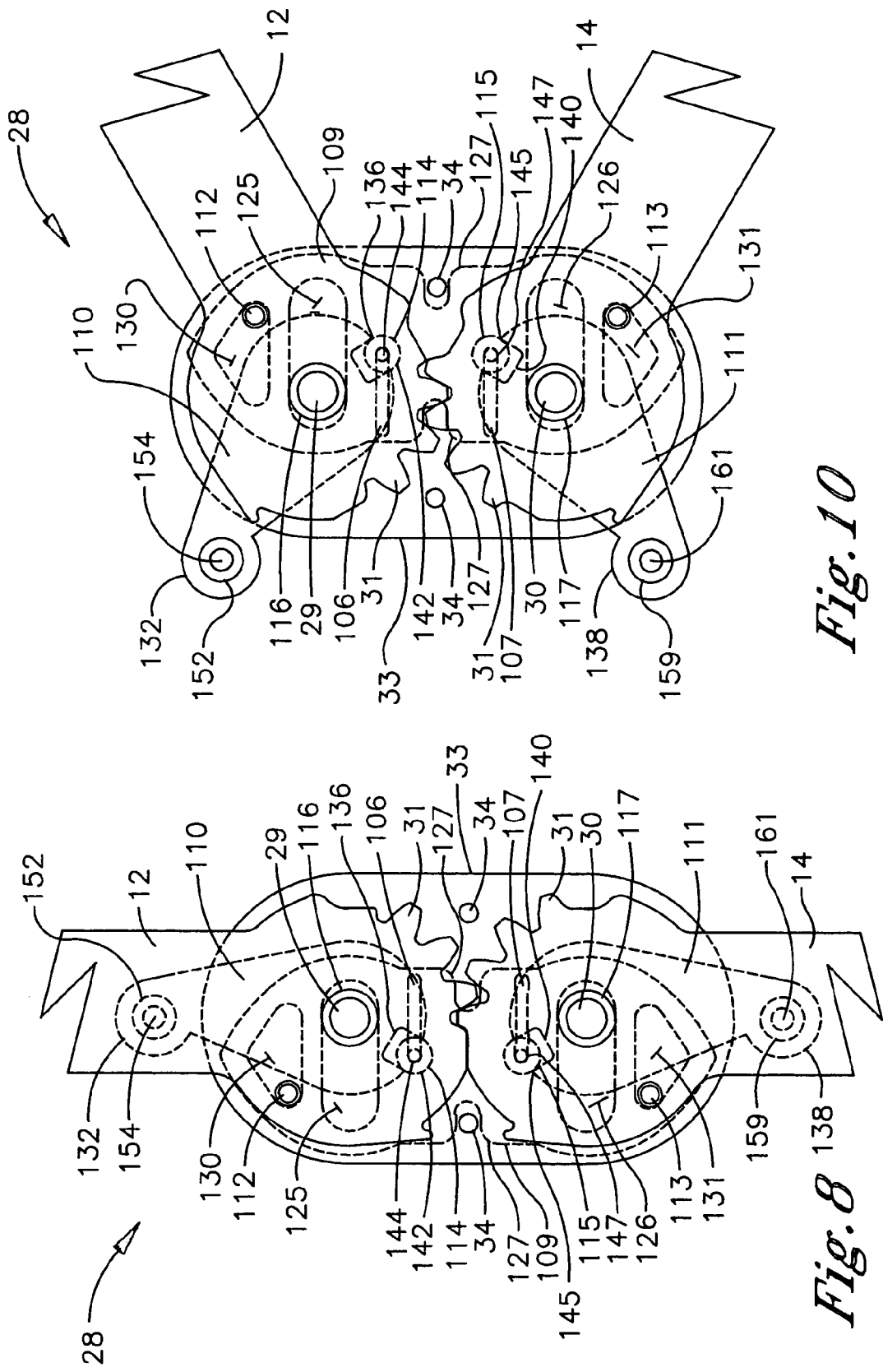

ORTHOSIS PROVIDING DYNAMIC TRACKING OF THE PATELLO-FEMORAL JOINT

This a continuation-in-part application of Ser. No. 09/669,061 filed on Sep. 22, 2000 now U.S. Pat. No. 6,551,264.

TECHNICAL FIELD

The present invention relates generally to knee orthoses, and more particularly to a knee orthosis which causes the patella to properly track the trochlear groove during movement of the knee.

BACKGROUND OF THE INVENTION

The patello-femoral joint of the knee is an articulation between the patella and femur. The joint consists of an articular surface on the posterior of the patella and a corresponding articular surface on the anterior of the head of the femur which is termed the trochlea. The posterior of the patella is contoured as a ridge, while the trochlea is contoured as a groove which is dimensioned to receive the patellar ridge in a complementary manner. Proper dynamic function of the patello-femoral joint requires that the patellar ridge accurately track the underlying trochlear groove when the knee is moved through flexion or extension. The anatomy and function of the patello-femoral joint are well known and described in detail in Ficat, R. P. et al., *Disorders of the Patello-femoral Joint*, Williams & Wilkins, 1977.

Functional disorders of the patello-femoral joint frequently relate to improper dynamics. Less severe forms of patello-femoral joint disorder cause pain in the joint, but do not exhibit errors in patellar tracking of the trochlear groove. In more severe forms of patello-femoral joint disorder, patellar tracking errors are evident in addition to joint pain, but there is no subluxation or dislocation of the joint. In still more severe forms of patello-femoral joint disorder, patellar tracking errors result in subluxation or dislocation of the joint. Recurrent subluxation of the patello-femoral joint is a particular disorder whereby the patella deviates transiently and typically rapidly from its normal axis of movement due to patellar tracking errors during movement of the knee. Slight deviations of the patella from its normal axis of movement are termed minor subluxation and may not produce any clinically apparent relocation of the patella. Minor subluxation is often the result of a functional imbalance in the knee. Significant deviations of patellar movement which approach dislocation are termed major subluxation. Major subluxation can be brought on by strenuous activity although it often occurs even in the absence of such activity. Recurrent patellar subluxation, both major and minor, is a relatively frequent condition among women generally and particularly among women athletes.

Most instances of subluxation or dislocation of the patella due to patellar-tracking errors are in the lateral direction because biomechanical forces typically bias the patella laterally when the knee is load-bearing. In addition, subluxation or dislocation of the patella due to patellar tracking errors has the greatest risk of occurring when the knee is approaching extension. When the knee ranges between about 30° of full extension and full extension, the trochlear groove becomes relatively small and shallow which is conducive to subluxation or dislocation. Functional disorders of the patello-femoral joint are highly undesirable because such disorders may ultimately lead to cartilage damage and arthritis of the knee. Therefore, a recognized need exists for effective preventative or remedial treatment of patello-femoral joint disorders.

It is an object of the present invention to provide a knee orthosis which prevents or remediates functional disorders of the patello-femoral joint including recurrent patellar subluxation or dislocation. More particularly, it is an object of the present invention to provide a knee orthosis which reduces the risk of patellar tracking errors by providing the knee with a patellar tracking guide. It is a specific object of the present invention to provide a knee orthosis which applies a patellar tracking guide to the head of the femur laterally or medially adjacent to the patella to reduce the risk of recurrent lateral or medial patellar subluxation or dislocation. It is a further object of the present invention to provide a knee orthosis having a patellar tracking guide which dynamically tensions when the knee approaches the extension position for maximum effect and dynamically relaxes when the knee approaches the flexion position to minimize interference with the function of the knee. It is still a further object of the present invention to provide a knee orthosis having a patellar tracking guide which is dynamically positioned more proximal to the patella when the knee approaches the extension position for maximum effect and is dynamically positioned more distal to the patella when the knee approaches the flexion position to minimize interference with the function of the knee. These objects and others are accomplished in accordance with the invention described hereafter.

SUMMARY OF THE INVENTION

The present invention is an orthosis mountable on a knee having a femoral head and patella. The orthosis comprises first upper and lower arms positionable about the knee and a first hinge assembly positioned between the first upper and lower arms and positionable at the knee to one side of the patella. The first hinge assembly comprises a lower end of the first upper arm, an upper end of the first lower arm, a tension strap lever including a tension strap connection point and a hinge pivot rotationally engaging the lower and upper ends of the first upper and lower arms, respectively, and the tension strap lever. The first upper and lower arms and the tension strap lever are rotatable about the hinge pivot to transition between a flexion position and an extension position. The orthosis may further comprise second upper and lower arms and a second hinge assembly positioned at the knee to the opposite side of the patella from the first arms and first hinge assembly. A substantially flexible tubular sleeve is provided to retain the upper and lower arms in relation to the knee. Alternatively, a stiffened upper cuff is provided to retain the upper arms and a stiffened lower cuff is provided to retain the lower arms.

A compression member is positioned at the femoral head adjacent to the patella on the opposite side of the patella from the first hinge assembly. In accordance with one embodiment, the compression member comprises a tracking guide engaging the knee and a compression plate in overlying engagement with the tracking guide. The compression plate is formed from a more rigid material than the relatively pliant tracking guide. A tension strap is connected to the tension strap lever at the tension strap connection point and is additionally connected to the compression member.

When the first upper and lower arms and tension strap lever rotationally transition from the flexion position to the extension position, the tension strap connection point is posteriorly displaced relative to the hinge pivot more distal from the patella, thereby increasing the tension force applied to the compression member. Conversely, when the first upper and lower arms and tension strap lever rotationally transition from the extension position to the flexion position, the tension strap connection point is anteriorly displaced relative to the hinge pivot more proximal to the patella, thereby decreasing the tension force applied to the compression member. The orthosis is further provided with a counterbalance connector connected to the compression member and oriented counter to the tension strap.

The present orthosis enables a method for maintaining proper tracking of the patella relative to the femoral head during range of motion movement of the knee. The method is initiated by placing the compression member in engagement with the knee at a location on the femoral head adjacent to the patella. The compression member is aligned with a desired dynamic patellar track. Range of motion movement is then performed on the knee by moving the knee from a flexion position to an extension position or from an extension position to a flexion position while applying a tension force to the compression member by the tension strap. The tension force increases when the tension strap connection point is posteriorly displaced away from the patella by the first hinge assembly as the knee approaches the extension position. Conversely, the tension force decreases when the tension strap connection is anteriorly displaced toward from the patella by the first hinge assembly as the knee approaches the flexion position. As such, the compression member presses against the femoral head with a variable tension force which enables the compression member to conform the patella to the desired dynamic patellar track during movement of the knee.

The present invention will be further understood from the drawings and the following detailed description.

BRIEF DESCRIPTION OF THE DRAWINGS

FIG. 1 is an anterior view of a knee orthosis of the present invention.

FIG. 2 is a lateral view of the knee orthosis of FIG. 1.

FIG. 3 is a posterior view of the knee orthosis of FIG. 1.

FIG. 4 is a medial view of the knee orthosis of FIG. 1.

FIGS. 6A and 6B are a detailed exploded perspective view of a hinge assembly of the present invention which is included within the knee orthosis of FIG. 1.

FIG. 7 is a medial view of the knee orthosis of FIG. 1 operatively positioned on the knee of a user with the knee in the extension position.

FIG. 8 is an operational medial view of the hinge assembly of FIGS. 6A and 6B with the knee in the extension position, wherein the outer and inner hinge plates are omitted from the hinge assembly for clarity of illustration.

FIG. 9 is a medial view of the knee orthosis of FIG. 1 operatively positioned on the knee of a user with the knee in the flexion position.

FIG. 10 is an operational medial view of the hinge assembly of FIGS. 6A and 6B with the knee in the flexion position, wherein the outer and inner hinge plates are omitted from the hinge assembly for clarity of illustration.

DESCRIPTION OF PREFERRED EMBODIMENTS

Figure 5:
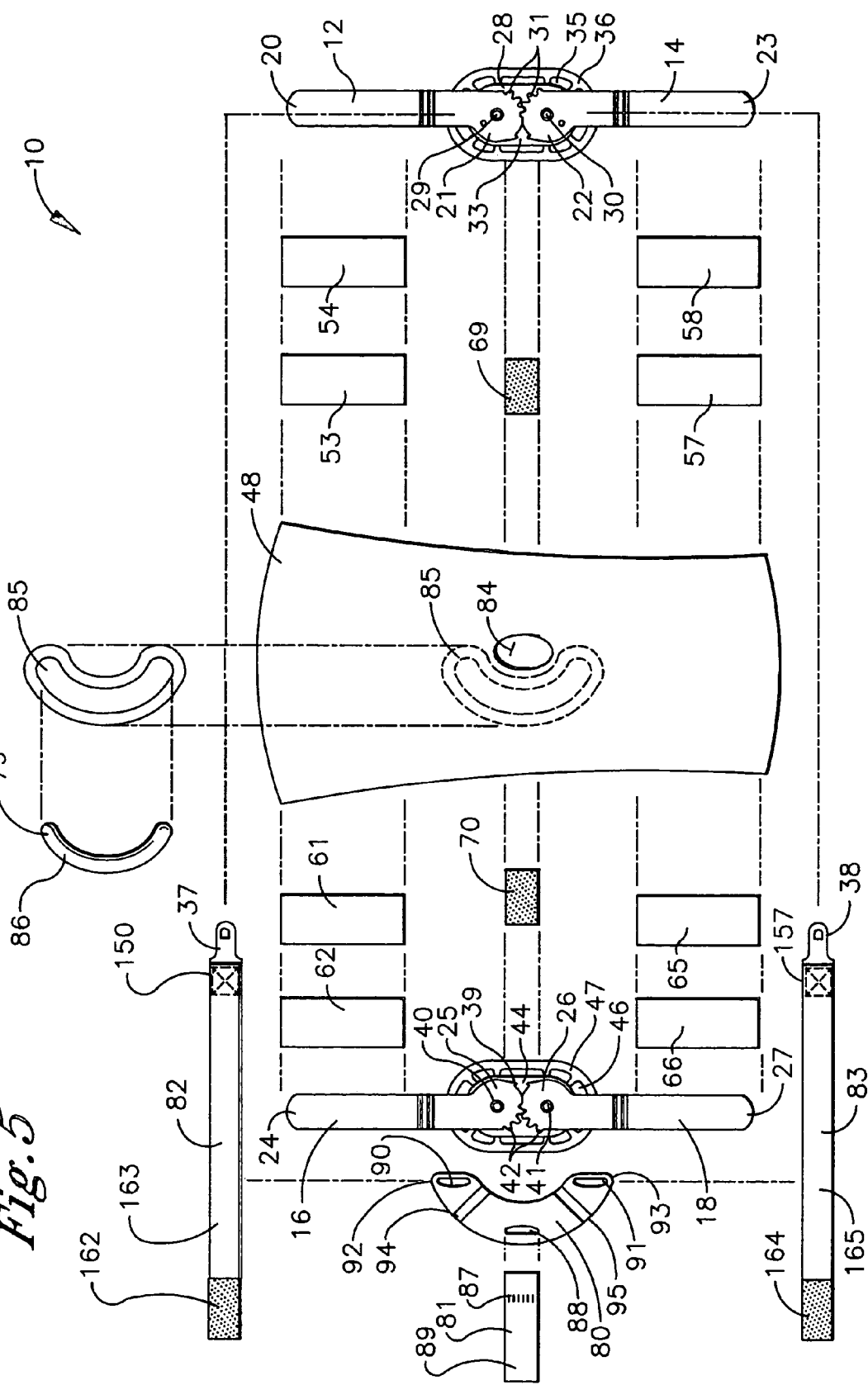
FIG. 5 is an exploded anterior view of the knee orthosis of FIG. 1, wherein the circumferential straps, outer hinge plates and details of the inner workings of the hinges are omitted for clarity of illustration.

Referring to FIGS. 1–5, the knee orthosis of the present invention is shown and generally designated 10. The positional terms, upper, lower, lateral, medial, anterior and posterior, are used herein with reference to the normal orientation of a knee on which the knee orthosis 10 is mounted in practice as described hereafter.

The knee orthosis 10 has a first pair of arms positioned on one side of the orthosis 10 and a second pair of arms positioned on the opposite side of the orthosis 10. The first pair of arms consists of a first upper arm 12 and a first lower arm 14. The second pair consists of a second upper arm 16 and a second lower arm 18. The first upper arm 12 defines an upper end 20 and a lower end 21, the first lower arm 14 defines an upper end 22 and a lower end 23, the second upper arm 16 defines an upper end 24 and a lower end 25, and the second lower arm 18 defines an upper end 26 and a lower end 27. The arms 12, 14, 16, 18 each have a bar-shaped configuration which provides the arms 12, 14, 16, 18 with semi-rigid flexibility characteristics. In particular, the arms 12, 14, 16, 18 each have a relatively larger dimension of width providing substantial inflexibility in the anterior and posterior directions and have a relatively smaller dimension of thickness providing a degree of flexibility in the medial and lateral directions. As such, each arm 12, 14, 16, 18 may be formed from the following types of materials which are well-known to those skilled in the art of hinged orthopedic knee braces: metals, fiberglass, graphite, resins, plastics, composites and combinations thereof.

The first pair of arms 12, 14 is provided with a first hinge assembly 28, which rotationally connects the lower end 21 of the first upper arm 12 and the upper end 22 of the first lower arm 14 about a first hinge pivot. The first hinge assembly 28 is a termed a polycentric hinge assembly because the first hinge pivot has two distally separate pivot elements 29, 30, which enable cooperative rotation of the first upper arm 12 and the first lower arm 14 about two distally separate centers of rotation. In particular, the first hinge pivot has a first upper pivot element 29 positioned at an upper center of rotation, about which the first upper arm 12 rotates, and a first lower pivot element 30 positioned at a lower center of rotation, about which the first lower arm 14 rotates. The first upper and lower pivot elements 29, 30 are each preferably a conventional rivet extending through the first hinge assembly 28. Although not shown, the first upper and lower pivot elements are alternatively rivets of the type disclosed in commonly-owned U.S. Pat. No. 5,807,294, incorporated herein by reference, which include first and second adjustment members, respectively, for concurrent treatment of osteoarthritis.

Cooperative rotation of the first upper arm 12 and the first lower arm 14 in unison about the first hinge pivot is enabled by a plurality of intermeshing teeth 31 formed on the lower end 21 of the first upper arm 12 and the upper end 22 of the first lower arm 14, respectively. The first hinge assembly 28 is substantially rigid except the upper and lower ends 20, 23 extending away from the first hinge assembly 28, which are semi-rigid, having a limited degree of flexibility as described above. Exemplary polycentric hinge assemblies are disclosed in above-recited U.S. Pat. No. 5,807,294 as well as commonly-owned U.S. Pat. No. 5,772,618, incorporated herein by reference.

In addition to the first upper and lower pivot elements 29, 30, the lower and upper ends 21, 22, and the intermeshing teeth 31 formed thereon, the first hinge assembly 28 further comprises a first outer hinge plate 32, a first condyle plate 33, and a plurality of hinge fasteners 34. The first outer hinge plate 32 is an oval-shaped structure forming the outside face of the first hinge assembly 28, which is distal to the user. The first condyle plate 33 is a similarly oval-shaped structure having substantially the same dimensions as the first outer hinge plate 32. The first condyle plate 32 forms the inside face of the first hinge assembly 28 opposite the first outer hinge plate 32 more proximal to the user. The first outer hinge plate 32 and first condyle plate 33 shield the inner workings of the first hinge assembly 28, which are positioned between the plates 32, 33, from the environment to avoid external interference during operation. The hinge fasteners 34 extend through the first hinge assembly 28 from the first outer hinge plate 32 to the first condyle plate 33 and cooperate with the first upper and lower pivot elements 29, 30 to maintain proper positioning of the components of the first hinge assembly 28. The hinge fasteners 34 are preferably conventional threaded screws.

A first condyle cup 35 is optionally positioned adjacent to the first condyle plate 33 and connected to the first hinge assembly 28 by means of fasteners, adhesives or the like. The first condyle cup 35 is formed from a stiffened material, such as a conventional plastic, which has a plurality of flexion slits are formed in its periphery, as disclosed in above-recited U.S. Pat. No. 5,807,294, to enhance the flexibility thereof. The first condyle cup 35 has a concave configuration to receive the condyle projecting from the knee of a user. A first condyle pad 36 is fitted in the first condyle cup 35 and attached thereto to cushion the knee condyle from the stiffened first condyle cup 35. Attachment of the first condyle pad 36 to the first condyle cup 35 is effected in a substantially permanent manner by conventional means, such as an adhesive, or in a selectively detachable manner by conventional means such as releasable hook and loop fasteners commercially available under the trade name "VELCRO". The first condyle pad 36 is a thickened continuous cushion formed from a conventional pliant padding material, such as a foam, or is alternatively a fluid-containing cushion, such as a pneumatic bladder. The first condyle cup 35 and associated first condyle pad 36 improve the fit, function and comfort of the knee orthosis 10 during use. The position of the first condyle cup 35 and associated fluid condyle pad 36 are adjustable relative to the knee of the user in accordance with the teaching of above-recited U.S. Pat. No. 5,807,294 if first and second adjustment members are provided with the first upper and lower pivot elements.

The first hinge assembly 28 is further provided with an upper tension strap connector 37 and a lower tension strap connector 38. The upper tension strap connector 37 and the lower tension strap connector 38 extend outwardly from the inner workings of the first hinge assembly 28 and are releasably connected thereto. The upper and lower tension strap connectors 37, 38 are identically configured and are constructed from a high-strength, relatively flexible material such as a plastic. The upper and lower tension strap connectors 37, 38 contribute to the function of the first hinge assembly 28 in cooperation with the innerworkings thereof. Further details of the upper and lower tension strap connectors 37, 38, the inner workings of the first hinge assembly 28, and their method of operation are described hereafter with reference to additional figures.

With continuing reference to FIGS. 1–5, the second pair of arms 16, 18 are provided with a second hinge assembly 39, which rotationally connects the lower end 25 of the second upper arm 16 and the upper end 26 of the second lower arm 18 about a second hinge pivot. The second hinge assembly 39 is preferably a polycentric hinge assembly as described above, but absent the inner workings of the first hinge assembly 28. As such, the second hinge assembly 39 includes a second upper pivot element 40, a second lower pivot element 41, second intermeshing teeth 42, a second outer hinge plate 43, a second condyle plate 44, second hinge fasteners 45, a second condyle cup 46, and a second condyle pad 47, which cooperatively function in a conventional manner. Alternatively, other conventional hinge assemblies within the purview of the skilled artisan may be substituted for the second hinge assembly 39 disclosed herein. For example, the second hinge assembly may have a single pivot element providing a single center of rotation, about which both the second upper and lower arms 16, 18 rotate, as disclosed in commonly-owned copending U.S. patent application Ser. No. 09/669,061, incorporated herein by reference.

The knee orthosis 10 has a tubular sleeve 48 formed from an elastic material, such as a breathable or non-breathable fabric-covered foam. The elastic sleeve 48 is highly flexible and stretchable, flexing and stretching to conform to the contours of a knee over which the sleeve 48 is fitted as described hereafter. The radial inwardly-directed elastic compression force of the sleeve 48 resists displacement of the sleeve 48 relative to the knee when the sleeve 48 is fitted over the knee. The sleeve 48 is provided with a first upper arm pocket 49, a first lower arm pocket 50, a second upper arm pocket 51, and a second lower arm pocket 52 parallely aligned with the longitudinal axis of the sleeve 48. The first upper and lower arm pockets 49, 50 are sized and positioned to engage and enclose the upper end 20 of the first upper arm 12 and the lower end 23 of the first lower arm 14, respectively. The second upper and lower arm pockets 51, 52 are sized and positioned to engage the upper end 24 of the second upper arm 16 and the lower end 27 of the second lower arm 18, respectively. As such, the first upper and lower arm pockets 49, 50 maintain the position of the first pair of arms 12, 14 and first hinge assembly 28 relative to the sleeve 48. The second upper and lower arm pockets 51, 52 similarly maintain the position of the second pair of arms 16, 18 and second hinge assembly 39 relative to the sleeve 48.

The first upper arm pocket 49 is formed by sewing a length of a first upper backing 53 onto the sleeve 48 and sewing a corresponding length of a first upper covering 54 onto the first upper backing 53 and sleeve 48. The length of the first upper backing 53 and first upper covering 54 each correspond to the length of the upper end 20. A first lower opening 55 is maintained in a first upper seam 56 joining the first upper covering 54 to the first upper backing 53 and the sleeve 48. The first lower opening 55 receives the upper end 20 of the first upper arm 12. The first lower arm pocket 50 is similarly formed by sewing lengths of a first lower backing 57 and a first lower covering 58 onto the sleeve 48, which each correspond to the length of the lower end 23. A first upper opening 59 is maintained in a first lower seam 60 which receives the lower end 23 of the first lower arm 14.

The second upper arm pocket 51 is formed by sewing lengths of a second upper backing 61 and a second upper covering 62 onto the sleeve 48, which each correspond to the length of the upper end 24. A second lower opening 63 is maintained in a second upper seam 64 which receives the upper end 24 of the second upper arm 16. The second lower arm pocket 52 is formed by sewing lengths of a second lower backing 65 and a second lower covering 66 onto the sleeve 48, which each correspond to the length of the lower end 27. A second upper opening 67 is maintained in a second lower seam 68, which receives the lower end 27 of the second lower arm 18.

A first condyle sleeve fastener 69, preferably a "VELCRO" releasable hook and loop fastener, is mounted on the central region of the sleeve 48 substantially between the first upper and lower arm pockets 49, 50. A corresponding first condyle pad fastener (not shown) is mounted on the face of the first condyle pad 36 proximal to the user. The first condyle sleeve fastener 69 is positioned such that it is aligned with the corresponding first condyle pad fastener when the first upper and lower arms 12, 14 are in place within the first upper and lower arm pockets 49, 50, respectively. A second condyle sleeve fastener 70 is similarly mounted on the central region of the sleeve 48 substantially between the second upper and lower arm pockets 51, 52. A corresponding second condyle pad fastener (not shown) is mounted on the face of the second condyle pad 47 proximal to the user. The second condyle sleeve fastener 70 is positioned such that it is aligned with the corresponding second condyle pad fastener when the second upper and lower arms 16, 18 are in place within the second upper and lower arm pockets 51, 52, respectively.

A plurality of circumferential straps 71, 72, 73, 74 are provided to secure the knee orthosis 10 to the knee and counterbalance rotation of the first and second hinge assemblies 28, 39. The circumferential straps 71, 72, 73, 74 are formed from a fabric which is flexible, but substantially non-stretchable. The circumferential strap 71 is an upper anterior strap which extends anteriorly between the upper ends 20, 24 of the first and second upper arms 12, 16, respectively, and has an orientation substantially perpendicular to the longitudinal axis of the sleeve 48. The upper anterior strap 71 is secured by attaching one end 75 of the strap 71 to the sleeve 48 adjacent to the upper end 24 and threading the other end 76 of the strap 71 through a rigid circumferential strap loop 77 fixedly attached to the sleeve 48 adjacent to the upper end 20. The end 76 of the strap 71 is fitted with a releasable fastener and the strap 71 has a mid-section 78 which is correspondingly fitted with a cooperative releasable fastener. The cooperative releasable fasteners of the end 76 and mid-section 78 are preferably conventional "VELCRO" releasable hook and loop fasteners. The length of the strap 71, is adjustable by overlapping the end 76 and the mid-section 78, selectively positioning the end 76 at a point on the mid-section 78, and releasably fastening the end 76 to the mid-section 78 at the selected point.

The circumferential strap 72 is an upper posterior strap which has a construction substantially similar to that of the upper anterior strap 71, but which extends posteriorly between the upper ends 20, 24 of the first and second upper arms 12, 16, respectively. The upper posterior strap 72 has a substantially perpendicular orientation relative to the longitudinal axis of the sleeve 48 and is adjustably secured in substantially the same manner as described above with respect to the upper anterior strap 71. The circumferential strap 73 is a lower posterior strap which has a construction substantially similar to that of the upper anterior strap 71, but which extends posteriorly between the lower ends 23, 27 of the first and second lower arms 14, 18, respectively. The lower posterior strap 73 is oriented and adjustably secured in substantially the same manner as the upper anterior strap 71. The circumferential strap 74 is a lower anterior strap which has a construction substantially similar to that of the upper anterior strap 71, but which extends anteriorly between the lower ends 23, 27 of the first and second lower arms 14, 18, respectively. The lower anterior strap 74 is oriented and adjustably secured in substantially the same manner as the upper anterior strap 71. Although not shown, it is apparent to the skilled artisan that one or more of the circumferential straps 71, 72, 73, 74 can alternatively be designed to circumscribe the entire sleeve 48, rather than only the anterior or posterior portion of the sleeve 48.

The knee orthosis 10 is further provided with a patellar tracking assembly which comprises a tracking guide 79, a compression plate 80, a counterbalance connector 81, an upper tension strap 82, a lower tension strap 83, the upper tension strap connector 37 and the lower tension strap connector 38. The tracking guide 79 and compression plate 80 are cooperatively positioned adjacent to a patellar opening 84 formed in the anterior side of the sleeve 48. The patellar opening 84 is shaped in correspondence with the periphery of a patella. A guide pocket 85 is sewn into the fabric of the sleeve 48 adjacent to the patellar opening 84. The guide pocket 85 and tracking guide 79 are correspondingly arcuately configured with the tracking guide 79 fitted into and retained within the guide pocket 85. The tracking guide 79 is formed from a flexible material such as a neoprene foam and preferably has a substantially rounded cross section, for the comfort of the user. In general, the material of the tracking guide 79 is substantially less rigid than the material of the compression plate 80 described hereafter, yet is substantially thicker, more dense, less compressible, and less stretchable than the material of the sleeve 48.

The compression plate 80 has an arcuate anterior profile substantially corresponding to that of the tracking guide 79 and has a relatively thin sheet-like elevational profile. The compression plate 80 is constructed from a relatively rigid material, such as a metal or a plastic, e.g., nylon. The compression plate 80 is positioned against the anterior face 86 of the tracking guide 79 in overlapping engagement with the tracking guide 79 and the overlying guide pocket 85.

The counterbalance connector 81 connects the compression plate 80 to the second hinge assembly 39 in a releasable, adjustable manner. The counterbalance connector 81 of the present embodiment is a connector strap constructed from a fabric which is flexible, but substantially non-stretchable. The anterior and posterior faces of the connector strap 81 are fitted with releasable fasteners. The fasteners are preferably conventional "VELCRO" releasable hook and loop fasteners integral with the connector strap 81. The connector strap 81 is substantially permanently connected to the compression plate 80 by threading an end 87 of the connector strap 81 through a connector strap slot 88 of the compression plate 80 and sewing the end 87 back onto of the connector strap 81. The connector strap slot 88 is formed through the compression plate 80 at the longitudinal midpoint of the compression plate 80. The opposite end 89 of the connector strap 81 is posteriorly directed from the connector strap slot 88 by threading the end 89 between the second hinge assembly 39 and the central region of the sleeve 48, upon which the condyle sleeve fastener 70 is mounted, to the posterior of the sleeve 48. The connector strap 81 is releasably and adjustably attached to the second hinge assembly 39 and the sleeve 48 by means of the fasteners on the opposite faces of the connector strap 81 and the second condyle pad fastener and the second condyle sleeve fastener 70, respectively.

Although a preferred embodiment of the counterbalance connector 81 is described above and shown in the drawing, it is understood that the present invention is not limited to a specific embodiment of the counterbalance connector. The present invention encompasses counterbalance connectors having alternate connective structures or locations of connection within the purview of the skilled artisan which maintain a static counter force on the compression plate 80 in a direction opposite the first hinge assembly 28 and opposing the tension force of the upper and lower tension straps 82, 83 described hereafter. For example, the counterbalance connector may be a connector strap having one end attached to the compression plate 80 in substantially the same manner as described above, but having the opposite end attached to a different component of the second hinge assembly 39 and/or a different region of the sleeve 48. The counterbalance connector may alternately be a substantially permanent fastener, such as a rivet or screw, which fastens the compression plate 80 directly to a location on the orthosis 10 at or proximal, preferably anterior, to the second hinge assembly 39. In yet another alternative, the counterbalance connector may be a connector strap having one end attached to the compression plate 80 in substantially the same manner as described above, but having the opposite end looped from the compression plate 80 posteriorly around the orthosis to the first hinge assembly 28 and attached at or proximal thereto. This embodiment of the counterbalance connector has particular utility where the orthosis includes the first upper and lower arms 12, 14 and the first hinge assembly 28, but excludes the second upper and lower arms 16, 18 and the second hinge assembly 39.

The upper and lower tension straps 82, 83, like the connector strap 81, are constructed from a fabric which is flexible, but substantially non-stretchable. The upper and lower tension straps 82, 83 are each releasably and adustably connected to the first hinge assembly 28 utilizing the upper and lower tension strap connectors 37, 38, respectively. The upper and lower tension straps 82, 83 are also each releasably and adustably connected to the compression plate 80 utilizing upper and lower tension strap slots 90, 91, respectively, which are formed through opposite upper and lower ends 92, 93 of the compression plate 80. In addition to the connector strap slot 88 and upper and lower tension strap slots 90, 91, an upper notch 94 and a lower notch 95 are formed latitudinally in the compression plate 80 adjacent to the upper and lower tension strap slots 90, 91, respectively. The upper and lower notches 94, 95 are depressions in the thickness of the compression plate 80, which provide the compression plate 80 with increased flexion at the position of the notches 94, 95. Connection of the upper and lower tension straps 82, 83 to the compression plate 80 and to the first hinge assembly 28 is described in greater detail below with reference to FIGS. 6A and 6B in addition to FIGS. 1–5.

Figure 6B:
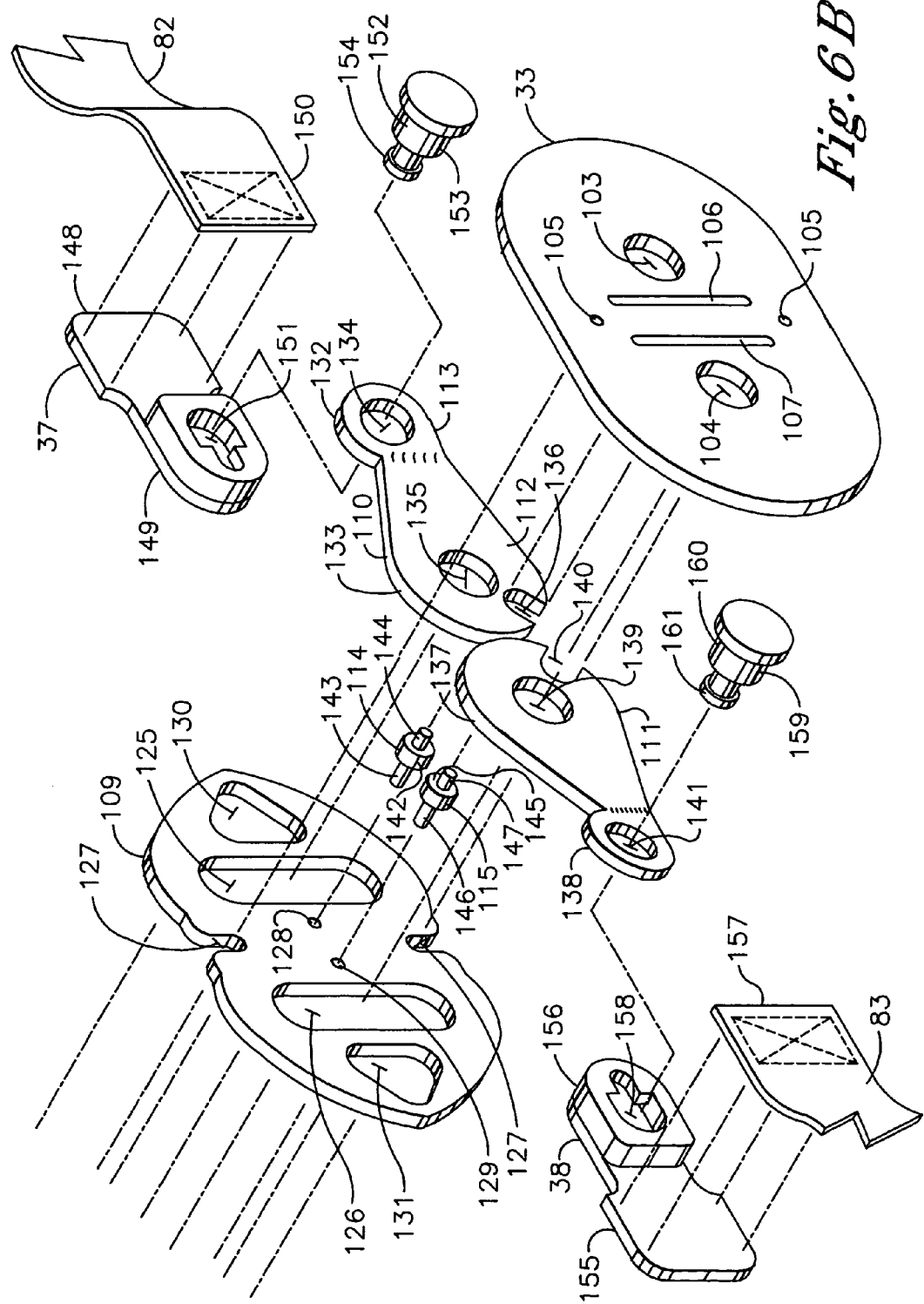

FIGS. 6A and 6B show the lower end 21 of the first upper arm 12, the upper end 22 of the first lower arm 14, the first upper and lower pivot elements 29, 30, the first teeth 31, the first outer hinge plate 32, the first condyle plate 33, the first hinge fasteners 34, the upper and lower tension strap connectors 37, 38 and the upper and lower tension straps 82, 83, which are described generally above and are described in further detail hereafter. The lower end 21 has an upper arm pivot aperture 96 and an upper arm drive peg aperture 97 formed therethrough. The upper end 22 correspondingly has a lower arm pivot aperture 98 and a lower arm drive peg aperture 99 formed therethrough. The first outer hinge plate 32 has upper and lower outer hinge plate pivot apertures 100, 101 and outer hinge plate fastening apertures 102 formed therethrough. The first condyle plate 33 correspondingly has upper and lower condyle plate pivot apertures 103, 104 and condyle plate fastening apertures 105 formed therethrough. The first condyle plate 33 further has upper and lower condyle plate drive bushing slots 106, 107 formed therethrough.

In addition to the above-recited components, FIGS. 6A and 6B further show the inner workings of the first hinge assembly 28, including an inner hinge plate 108, a drive plate 109, an upper tension strap lever 110, a lower tension strap lever 111, an upper drive peg 112, a lower drive peg 113, an upperdrive bushing 114, a lower drive bushing 115, an upper pivot bushing 116 and a lower pivot bushing 117. The inner workings of the first hinge assembly 28 are constructed from one or more high-strength relatively rigid materials, such as metals and the like.

The inner hinge plate 108 is an oval-shaped structure having substantially the same dimensions as the first outer hinge plate 32 and first condyle plate 33. The inner hinge plate 108 has upper and lower inner hinge plate pivot apertures 118, 119 and inner hinge plate fastening apertures 120 formed therethrough. The inner hinge plate 108 further has upper and lower inner hinge plate drive bushing slots 121, 122 and upper and lower inner hinge plate drive peg slots 123, 124 formed therethrough. The drive plate 109 is an irregular-shaped structure having a substantially smaller profile than the first outer hinge plate 32, first condyle plate 33 and inner hinge plate 108, such that the drive plate 109 is linearly slidably displaceable between the first outer hinge plate 32 and the inner hinge plate 108 without extending past the edges of the plates 32, 108. The drive plate 109 has upper and lower drive plate pivot slots 125, 126 and drive plate fastener by-pass notches 127 formed therethrough. The drive plate 109 further has upper and lower drive plate drive bushing apertures 128, 129 and upper and lower drive plate drive peg apertures 130, 131 formed therethrough.

The upper and lower tension strap levers 110, 111 each have essentially the same construction. The upper tension strap lever 110 has a tapered upper external end 132 and a widened lower internal end 133. The upper tension strap lever 110 is rotationally displaceable about the first upper pivot element 29 and upper pivot bushing 116 relative to the first outer hinge plate 32, inner hinge plate 108, and first condyle plate 33 during operation of the first hinge assembly 28 as described below. However, the lower internal end 133 remains between the first outer hinge plate 32 and the inner hinge plate 108 internal thereto at all times without extending past the edges of the plates 32, 108 during operation. In contrast, the upper external end 132 extends outside the edges of the first outer hinge plate 32 and the inner hinge plate 108 external thereto at all times during operation. The upper external end 132 has an upper lever anchor aperture 134 formed therethrough. The lower internal end 133 has an upper lever pivot aperture 135 and an upper lever drive bushing notch 136 formed therethrough.

The lower tension strap lever 111 is likewise rotationally displaceable about the first lower pivot element 30 and lower pivot bushing 117 relative to the first outer hinge plate 32, inner hinge plate 108, and first condyle plate 33 during operation of the first hinge assembly 28 and correspondingly has a widened upper internal end 137 and a lower tapered external end 138. The upper internal end 137 remains between the first outer hinge plate 32 and the inner hinge plate 108 internal thereto at all times while the lower external end 138 extends outside the edges of the first outer hinge plate 32 and the inner hinge plate 108 external thereto at all times during operation. The upper internal end 137 has a lower lever pivot aperture 139 and a lower lever drive bushing notch 140 formed therethrough. The lower external end 138 has a lower lever anchor aperture 141 formed therethrough.

Although it is apparent to the skilled artisan that the invention is not limited to any one specific sequential order of components within the first hinge assembly 28, a preferred sequence of components is shown herein, which proceeds proximally in the direction of the knee of a user as follows: the first outer hinge plate 32, the lower and upper ends 21, 22 of the first upper and lower arms 12, 14, respectively, the inner hinge plate 108, the drive plate 109, the upper and lower tension strap levers 110, 111, and the first condyle plate 33. The first outer hinge plate 32, upper end 21, inner hinge plate 108, drive plate 109, upper tension strap lever 110, and first condyle plate 33 are oriented relative to each other such that the upper outer hinge plate pivot aperture 100, upper arm pivot aperture 96, upper inner hinge plate pivot aperture 118, upper drive plate pivot slot 125, upper lever pivot aperture 135, and upper condyle plate pivot aperture 103 are all in alignment with one another to receive the first upper pivot element 29 and concentric upper pivot bushing 116 therethrough.

The diameter of the upper pivot bushing 116 is correspondingly sized such that the upper pivot bushing 116 is relatively closely fitted within the upper outer hinge plate pivot aperture 100, upper arm pivot aperture 96, upper inner hinge plate pivot aperture 118, upper lever pivot aperture 135, and upper condyle plate pivot aperture 103. In comparison, the upper drive plate pivot slot 125 is sized substantially larger than the diameter of the upper pivot bushing 116. As such, the upper pivot bushing 116 is slidably displaceable within the upper drive plate pivot slot 125 so that the upper pivot bushing 116 and first upper pivot element 29 do not impede linear slidable displacement of the drive plate 109 relative to the first outer hinge plate 32, upper end 21, inner hinge plate 108, upper tension strap lever 110, and first condyle plate 33. The first upper arm 12 and upper tension strap lever 110 are both rotationally displaceable about the upper arm pivot aperture 96, upper pivot bushing 116 and first upper pivot element 29 relative to the first outer hinge plate 32, inner hinge plate 108, and first condyle plate 33.

The first outer hinge plate 32, upper end 21, inner hinge plate 108, drive plate 109, upper tension strap lever 110, and first condyle plate 33 are likewise oriented such that the lower outer hinge plate pivot aperture 101, lower arm pivot aperture 98, lower inner hinge plate pivot aperture 119, lower drive plate pivot slot 126, lower lever pivot aperture 139, and lower condyle plate pivot aperture 104 are all in alignment with one another to receive the first lower pivot element 30 and concentric lower pivot bushing 117 therethrough. The diameter of the lower pivot bushing 117 is correspondingly sized such that the lower pivot bushing 117 is relatively closely fitted within the lower outer hinge plate pivot aperture 101, lower arm pivot aperture 98, lower inner hinge plate pivot aperture 119, lower lever pivot aperture 139, and lower condyle plate pivot aperture 104. In comparison, the lower drive plate pivot slot 125 is sized substantially larger than the diameter of the lower pivot bushing 117. As such, the lower pivot bushing 117 is slidably displaceable within the lower drive plate pivot slot 126 so that the lower pivot bushing 117 and first lower pivot element 30 do not impede linear slidable displacement of the drive plate 109 relative to the first outer hinge plate 32, lower end 22, inner hinge plate 108, lower tension strap lever 111, and first condyle plate 33. The first lower arm 14 and lower tension strap lever 111 are both rotationally displaceable about the lower arm pivot aperture 98, lower pivot bushing 117 and first lower pivot element 30 relative to the first outer hinge plate 32, inner hinge plate 108, and first condyle plate 33.

The first outer hinge plate 32, inner hinge plate 108, drive plate 109, and first condyle plate 33 are oriented such that the outer hinge plate fastening apertures 102, inner hinge plate fastening apertures 120, drive plate fastener by-pass notches 127, and condyle plate fastening apertures 105 are all in alignment with one another to receive the first hinge fasteners 34 therethrough. The diameter of the first hinge fasteners 34 are correspondingly sized such that the first hinge fasteners 34 are closely fitted within the outer hinge plate fastening apertures 102, inner hinge plate fastening apertures 120, and first condyle plate fastening apertures 105 to maintain the position of the first outer hinge plate 32, inner hinge plate 108, and first condyle plate 33 fixed relative to one another. In comparison, the drive plate fastener by-pass notches 127 are sized substantially larger than the diameter of the first hinge fasteners 34. As such, the first hinge fasteners 34 are slidably displaceable within the drive plate fastener by-pass notches 127 so that the first hinge fasteners 34 do not impede linear slidable displacement of the drive plate 109 relative to the first outer hinge plate 32, inner hinge plate 108, and first condyle plate 33.

The upper end 21, inner hinge plate 108, and drive plate 109 are oriented such that the upper arm drive peg aperture 97, upper inner hinge plate drive peg slot 123, and upper drive plate drive peg aperture 130 are all in alignment with one another to receive the upper drive peg 112 therethrough. The diameter of the upper drive peg 112 is correspondingly sized such that the upper drive peg 112 is relatively closely fitted within the upper arm drive peg aperture 97 and upper drive plate drive peg aperture 130. In comparison, the upper inner hinge plate drive peg slot 123 is sized substantially larger than the diameter of the upper drive peg 112. As such, the upper drive peg 112 is slidably displaceable within the upper inner hinge plate drive peg slot 123. Accordingly, the upper drive peg 112 effects linear slidable displacement of the drive plate 109 relative to the inner hinge plate 108 by means of fitted engagement with the upper arm drive peg aperture 97 and with the upper drive plate drive peg aperture 130 and by means of less restricted engagement with the upper inner hinge plate drive peg slot 123 when the first upper arm 12 is rotationally displaced.

The lower end 22, inner hinge plate 108, and drive plate 109 are likewise oriented such that the lower arm drive peg aperture 99, lower inner hinge plate drive peg slot 124, and lower drive plate aperture 131 are all in alignment with one another to receive the lower drive peg 113 therethrough. The diameter of the lower drive peg 113 is correspondingly sized such that the lower drive peg 113 is relatively closely fitted within the lower arm drive peg aperture 99 and lower drive plate drive peg aperture 131. In comparison, the lower inner hinge plate drive peg slot 124 is sized substantially larger than the diameter of the lower drive peg 113. As such, the lower drive peg 113 is slidably displaceable within the lower inner hinge plate drive peg slot 124. Accordingly, the lower drive peg 113 effects linear slidable displacement of the drive plate 109 relative to the inner hinge plate 108 by means of fitted engagement with the lower arm drive peg aperture 99 and with the lower drive plate drive peg aperture 131 and by means of less restricted engagement with the lower inner hinge plate drive peg slot 124 when the first lower arm 14 is rotationally displaced.

The inner hinge plate 108, drive plate 109, upper tension strap lever 110, and first condyle plate 33 are oriented such that the upper inner hinge plate drive bushing slot 121, upper drive plate drive bushing aperture 128, upper lever drive bushing notch 136, and upper condyle plate drive bushing slot 106 are all in alignment with one another to receive the upper drive bushing 114 therethrough. The upper drive bushing 114 is configured with a widened upper mid-section 142 and narrower upper first and second ends 143, 144. The diameter of the widened upper mid-section 142 is correspondingly sized such that the upper mid-section 142 is received by and relatively closely fitted within the upper lever drive bushing notch 136. The diameter of the narrower upper first end 143 is correspondingly sized such that the upper first end 143 is received by and relatively closely fitted within the upper drive plate drive bushing aperture 128.

In comparison, the upper inner hinge plate drive bushing slot 121 is sized substantially larger than the diameter of the upper first end 143. As such, the upper first end 143 is slidably displaceable within the upper inner hinge plate drive bushing slot 121. The upper condyle plate drive bushing slot 106 is sized substantially larger than the diameter of the upper second end 144. As such, the upper second end 144 is slidably displaceable within the upper condyle plate drive bushing slot 106. Accordingly, the upper drive bushing 114 effects rotational displacement of the upper tension strap lever 110 relative to the first outer hinge plate 32, inner hinge plate 108 and first condyle plate 33 by means of fitted engagement between the upper midsection 142 and upper lever drive bushing notch 136 and between the upper first end 143 and upper drive plate drive bushing aperture 128 and by means of less restricted engagement between the upper first end 143 and upper inner hinge plate drive bushing slot 121 and between the upper second end 144 and upper condyle plate drive bushing slot 106 when the drive plate 109 is linearly displaced.

The inner hinge plate 108, drive plate 109, lower tension strap lever 111, and first condyle plate 33 are likewise oriented such that the lower inner hinge plate drive bushing slot 122, lower drive plate drive bushing aperture 129, lower lever drive bushing notch 140, and lower condyle plate drive bushing slot 107 are all in alignment with one another to receive the lower drive bushing 115 therethrough. The lower drive bushing 115 is configured with a widened lower mid-section 145 and narrower lower first and second ends 146, 147. The diameter of the widened lower mid-section 145 is correspondingly sized such that the lower mid-section 145 is received by and relatively closely fitted within the lower lever drive bushing notch 140. The diameter of the narrower lower first end 146 is correspondingly sized such that the lower first end 146 is received by and relatively closely fitted within the lower drive plate drive bushing aperture 129.

In comparison, the lower inner hinge plate drive bushing slot 122 is sized substantially larger than the diameter of the lower first end 146. As such, the lower first end 146 is slidably displaceable within the lower inner hinge plate drive bushing slot 122. The lower condyle plate drive bushing slot 107 is sized substantially larger than the diameter of the lower second end 147. As such, the lower second end 147 is slidably displaceable within the lower condyle plate drive bushing slot 107. Accordingly, the lower drive bushing 115 effects rotational displacement of the lower tension strap lever 111 relative to the first outer hinge plate 32, inner hinge plate 108 and first condyle plate 33 by means of fitted engagement between the lower mid-section 145 and lower lever drive bushing notch 140 and between the lower first end 146 and lower drive plate drive bushing aperture 129 and by means of less restricted engagement between the lower first end 146 and lower inner hinge plate drive bushing slot 122 and between the lower second end 147 and lower condyle plate drive bushing slot 107 when the drive plate 109 is linearly displaced.

As noted above, the upper and lower tension strap connectors 37, 38 each have essentially the same construction and enable releasable connection of the upper and lower tension straps 82, 83, respectively, to the first hinge assembly 28. The upper tension strap connector 37 has an upper tension strap attachment portion 148 and an upper lever attachment portion 149 at opposite ends of the upper tension strap connector 37. The upper tension strap attachment portion 148 is a thin flat tab to which a first end 150 of the upper tension strap 82 is substantially permanently attached by means such as sewing, adhesion, or the like. The upper lever attachment portion 149 is a body having an upper receptacle 151, which is configured to selectively releasably and rotationally retain an upper anchor 152. The upper anchor 152 is in turn attached to the upper tension strap lever 110. A preferred configuration of the upper receptacle 151 and the upper anchor 152 and a preferred method of operating the same are disclosed in commonly-owned copending U.S. patent application Ser. No. 10/099,591 filed on Mar. 14, 2002, incorporated herein by reference.

In accordance with the teaching of the above-recited reference, the upper anchor 152 has a widened upper base portion 153 correspondingly sized to closely fit within the upper lever anchor aperture 134 and to be substantially permanently retained therein. The upper anchor 152 also has a narrower upper retention portion 154 sized to fit within the upper receptacle 151 and to be releasably retained therein. As such, the upper tension strap connector 37 effects releasable connection of the uppertension strap 82 to the first hinge assembly 28 by means of permanent attachment between the upper tension strap attachment portion 148 and first end 150 of the upper tension strap 82, releasable attachment between the upper receptacle 151 and upper retention portion 154, and permanent attachment between the upper lever anchor aperture 134 and upper base portion 153.

The lower tension strap connector 38 correspondingly has a lower tension strap attachment portion 155 and a lower lever attachment portion 156 at opposite ends of the lower tension strap connector 38. The lower tension strap attachment portion 155 is substantially permanently attached to a first end 157 of the lower tension strap 83 and the lower lever attachment portion 156 has a lower receptacle 158 configured to selectively releasably and rotationally retain a lower anchor 159, which in turn is attached to the lower tension strap lever 111. Like the upper anchor 152, the lower anchor 159 has a widened lower base portion 160 correspondingly sized to closely fit within the lower lever anchor aperture 141 and to be substantially permanently retained therein. The lower anchor 159 also has a narrower lower retention portion 161 sized to fit within the lower receptacle 158 and to be releasably retained therein. As such, the lower tension strap connector 38 effects releasable connection of the lower tension strap 83 to the first hinge assembly 28 by means of permanent attachment between the lower tension strap attachment portion 155 and first end 157 of the lower tension strap 83, releasable attachment between the lower receptacle 158 and lower retention portion 161, and permanent attachment between the lower lever anchor aperture 141 and lower base portion 160.

The upper tension strap 82 has a second end 162 and a mid-section 163 between the first and second ends 150, 162. The second end 162 and mid-section 163 are fitted with cooperative releasable fasteners, preferably conventional "VELCRO" releasable hook and loop fasteners. The upper tension strap 82 is connected to the compression plate 80 in an adjustable releasable manner by threading the second end 162 through the upper tension strap slot 90 of the compression plate 80. The length of the upper tension strap 82 is adjustable by overlapping the second end 162 back over the mid-section 163, selectively positioning the second end 162 at a point on the mid-section 163, and releasably fastening the second end 162 to the mid-section 163 at the selected point by means of the cooperative releasable fasteners. Thus, the upper tension strap 82 extends between the compression plate 80 and the first hinge assembly 28, and more particularly between the upper tension strap slot 90 of the compression plate 80 and the upper retention portion 154 of the upper anchor 152 on the upper tension strap lever 110 of the first hinge assembly 28 via the upper tension strap connector 37.

The lower tension strap 83 correspondingly has a second end 164 and a mid-section 165 between the first and second ends 157, 164. The second end 164 and mid-section 165 are fitted with cooperative releasable fasteners, preferably conventional "VELCRO" releasable hook and loop fasteners. The lower tension strap 83 is connected to the compression plate 80 in an adjustable releasable manner by threading the second end 164 through the lower tension strap slot 91 of the compression plate 80. The length of the lower tension strap 83 is adjustable by overlapping the second end 164 back over the mid-section 165, selectively positioning the second end 164 at a point on the mid-section 165, and releasably fastening the second end 164 to the mid-section 165 at the selected point by means of the cooperative releasable fasteners. Thus, the lower tension strap 83 extends between the compression plate 80 and the first hinge assembly 28, and more particularly between the lower retention portion 161 of the lower tension strap slot 91 of the compression plate 80 and the lower anchor 159 on the lower tension strap lever 111 of the first hinge assembly 28 via the lower tension strap connector 38.

It is apparent from the above-recited disclosure that the upper and lower tension straps 82, 83 provide a releasable and adjustable connection between the first hinge assembly 28 and the compression plate 80 by means of connection points 90, 91, 154, 161. Furthermore, the connection points 154, 161 move relative to the first upper and lower pivot elements 29, 30 during operation of the knee orthosis 10, which enables the desired utility of the knee orthosis as described below.

The first upper and lower arms 12, 14 of the first hinge assembly 28 and/or the second upper and lower arms 16, 18 of the second hinge assembly 39 may additionally be provided with fixed rotation stops 166 or adjustable rotation stops (not shown), which cooperate with additional stop elements (not shown) attached to the first hinge assembly 28 and/or second hinge assembly 39 in a conventional manner, to substantially prevent rotation of the knee orthosis past fixed or adjustably selected extension or flexion positions of rotation. Although the full extension position of the knee orthosis 10, as shown in FIGS. 1–8, is at a rotation angle of 180°, in practice the fixed rotation stops 166 of the second hinge assembly 39 preferably cooperate with additional stop elements attached to the second hinge assembly 39 to substantially prevent rotation of the knee orthosis 10 past a rotation angle of about 170°. As a result, the knee is not permitted to extend past about the final 10° of extension, thereby reducing the risk hyperextension of the knee when the knee orthosis 10 is operational as described hereafter.

Operation of the knee orthosis 10 is described with continuing reference to FIGS. 1–6B and further reference to FIGS. 7–10. The knee orthosis 10 is positioned on a knee 167 for which patellar stabilization is desired by pulling the sleeve 48 over the leg until the patellar opening 84 circumscribes the patella 168 of the knee 167 and the first and second condyle pads 36, 47 are appropriately positioned against the condyles of the knee 167. The user manually positions the tracking guide 79 at the lateral side of the femoral head adjacent to the patella 168 and trochlea behind the patella 168, taking care to insure that the tracking guide 79 does not overlap the patella 168. The user tightens the circumferential straps 71, 72, 73, 74 in a desired sequence while the knee 167 is in substantially full extension. The user then flexes the knee 167 at an angle of about 45° from full extension while maintaining the position of the tracking guide 79 at the lateral side of the femoral head and tightens the upper and lower tension straps 82, 83 at a selected strap length which exerts a desired tension force on the compression plate 80. The strap length is preferably maintained fixed during range of motion movement of the knee 167, but can be readjusted if needed by interrupting the range of motion movement and tightening or loosening the upper or lower tension straps 82, 83 to a desired degree while the knee orthosis 10 remains in place on the knee 167.

When the user performs range of motion movement on the knee 167, the knee orthosis 10 remediates existing patello-femoral joint disorders or precludes potential disorders by maintaining accurate patellar tracking of the trochlear groove to substantially prevent patellar subluxation or dislocation. Specifically, the upper and lower tension straps 82, 83 apply a tension force to the compression plate 80, which responds to the tension force by exerting a posteriorly-directed force against the tracking guide 79. Accordingly, the tension force presses and retains the tracking guide 79 in a self-adjusting position against the lateral side of the femoral head with the face of the tracking guide 79 adjoining, but not overlapping, the adjacent edge of the patella 168. The position of the tracking guide 79 enforces a desired patellar track by maintaining the patella 168 in the underlying trochlear groove and preventing the patella 168 from migrating in a lateral direction out of the trochlear groove when the knee 167 moves through its normal range of motion. By not overlapping the patella 168, the tracking guide 79 also substantially avoids radial compression of the patella 168 which would undesirably tend to inhibit normal range of motion of the knee 167 and cause pain to the user.

An advantageous feature of the knee orthosis 10 is the ability to self-adjust in response to changes in the position of the knee 167. In particular, the position of the tracking guide 79 relative to the knee 167 and the tension force which presses the tracking guide 79 against the femoral head are automatically self-adjusting as a function of the degree of flexion or extension of the knee 167. When the knee 167 approaches a position of full flexion, the tracking guide 79 is displaced away from the knee 167 and the force of the tracking guide 79 against the femoral head diminishes. However, when the knee 167 approaches a position of full extension, the tracking guide 79 is displaced toward the knee 167 and the force of the tracking guide 79 against the femoral head increases. Accordingly, the tracking guide 79 is more securely retained against the femoral head relatively proximal to the knee 167 when the risk of patellar subluxation or dislocation is greater, i.e., generally during the last 15° to 30° of knee extension, and less securely retained against the femoral head relatively distal from the knee 167 when the risk of patellar subluxation or dislocation is least, i.e., during substantial knee flexion.

The self-adjusting position and compression features of the knee orthosis 10 are illustrated with reference to FIGS. 7–10. Referring initially to FIG. 7, the knee orthosis 10 is mounted on the knee 167 with the orthosis 10 and the knee 167 in corresponding positions of substantially full extension. As such, the alignment angle β of the first upper and lower arms 12, 14 at substantially full extension is shown as 180° for purposes of illustration. In practice, the alignment angle β at substantially full extension may encompass angles less than 180° to about 170° since it is often desirable to limit full extension of the knee 167 to somewhat less than 180° for treatment purposes as noted above. Although not shown in FIG. 7, the second upper and lower arms 16, 18 also have an alignment angle substantially equal to the alignment angle β of the first upper and lower arms 12, 14.

When the knee orthosis 10 is in full extension, the first upper and lower arms 12, 14, the first hinge pivot (i.e., the first upper and lover pivot elements 29, 30), and the connection points 154, 161 of the upper and lower tension straps 82, 83 are all in essentially common vertical alignment with one another and the connection points 154, 161 are positioned relatively distal to the knee 167. Consequently, the upper and lower tension straps 82, 83 become more taut and the tension force which the upper and lower tension straps 82, 83 exert on the compression plate 80 increases.

Details of the inner workings of the first hinge assembly 28 when the first hinge assembly 28 is at full extension are described below with additional reference to FIG. 8, wherein the first outer hinge plate 32 and the inner hinge plate 108 are omitted for clarity of illustration. As noted above, however, the positions of the first outer hinge plate 32, inner hinge plate 108, and first condyle plate 33 are fixed relative to one another at all times during operation of the first hinge assembly 28. As such, the first outer hinge plate 32, inner hinge plate 108, and first condyle plate 33 are termed static components of the first hinge assembly 28. In contrast, the first upper and lower arms 12, 14, the drive plate 109, and the upper and lower tension strap levers 110, 111 are termed dynamic components of the first hinge assembly 28 insofar as the positions of the first upper and lower arms 12, 14, the drive plate 109, and the upper and lower tension strap levers 110, 111 vary during operation of the first hinge assembly 28. Accordingly, the position of the first condyle plate 33 relative to the first upper and lower arms 12, 14 and the drive plate 109 described below and shown in FIG. 8 also applies to the first outer hinge plate 32 and inner hinge plate 108 not shown in FIG. 8.

Placement of the first upper and lower arms 12, 14 of the first hinge assembly 28 in the extension position, effects a series of events within the first hinge assembly 28, which cause distal positioning of the connection points 154, 161 relative to the knee 167. In particular, placement of the upper and lower arms 12, 14 in the extension position determines the positions of the upper and lower drive pegs 112, 113 because the upper and lower drive pegs 112, 113 are retained in the upper and lower arm drive apertures 97, 99 of the lower and upper ends 21, 22 of the upper and lower arms 12, 14, respectively. The position of the upper and lower drive pegs 112, 113 correspondingly determines the position of the drive plate 109 because the drive plate 109 retains the upper and lower drive pegs 112, 113 in the upper and lower drive plate peg apertures 130, 131, respectively. The position of the drive plate 109 correspondingly determines the position of the upper and lower drive bushings 114, 115 because the upper and lower drive bushings 114, 115 are retained in the upper and lower drive plate drive bushing apertures 128, 129, respectively, of the drive plate 109. The position of the upper and lower drive bushings 114, 115 correspondingly determines the position of the upper and lower external ends 132, 138 of the upper and lower tension strap levers 110, 111, which have the connection points 154, 161 mounted thereon, because the upper and lower drive bushings 114, 115 are retained in the upper and lower lever drive bushing notches 136, 140, respectively, of the lower and upper internal ends 133, 137 of the upper and lower tension strap levers 110, 111.

Referring to FIG. 9, the knee orthosis 10 and knee 167 are shown in corresponding positions of flexion, which are effected by rotational displacement of the knee orthosis 10 and the knee 167 away from the positions of substantially full extension shown in FIG. 7. As such, the alignment angle β of the first upper and lower arms 12, 14 is decreased from about 180° to about 90°. Although not shown in FIG. 9, the alignment angle of the second upper and lower arms 16, 18 is likewise decreased to about 90°. Rotation of the knee orthosis 10 to flexion anteriorly displaces the connection points 154, 161 of the upper and lower tension straps 82, 83 relative to the first upper and lower pivot elements 29, 30, while posteriorly displacing the upper end 20 of the first upper arm 12 and the lower end 23 of the first lower arm 14. Accordingly, when the knee orthosis 10 is in flexion, the connection points 154, 161 extend anteriorly away from the vertical alignment with the first upper and lower pivot elements 29, 30, while the upper end 20 of the first upper arm 12 and the lower end 23 of the first lower arm 14 extend posteriorly away from the vertical alignment with the first upper and lower pivot elements 29, 30. Consequently, the upper and lower tension straps 82, 83 become more slack decreasing the tension force the upper and lower tension straps 82, 83 exert on the compression plate 80.

Details of the inner workings of the first hinge assembly 28 when the first hinge assembly 28 is at flexion are described below with additional reference to FIG. 10, wherein the first outer hinge plate 32 and the inner hinge plate 108 are omitted for clarity of illustration. Placement of the first upper and lower arms 12, 14 of the first hinge assembly 28 in the flexion position, effects a series of events within the first hinge assembly 28, which cause proximal positioning of the connection points 154, 161 relative to the knee 167. In particular, placement of the upper and lower arms 12, 14 in the flexion position posteriorly displaces the upper and lower drive pegs 112, 113 in correspondence with posterior rotational displacement of the lower and upper ends 21, 22 of the upper and lower arms 12, 14, respectively. Posterior displacement of the upper and lower drive pegs 112, 113 correspondingly posteriorly displaces the drive plate 109. Posterior displacement of the drive plate 109 correspondingly posteriorly displaces the upper and lower drive bushings 114, 115. Posterior displacement of the upper and lower drive bushings 114, 115 correspondingly rotationally displaces the lower and upper internal ends 133, 137 of the upper and lower tension strap levers 110, 111 and correspondingly anteriorly rotationally displaces the upper and lower external ends 132, 138 which have the connection points 154, 161 mounted thereon.

When the first hinge assembly 28 is transitioned from flexion back to extension, the above-recited series of events are reversed. In particular, return of the upper and lower arms 12, 14 to the extension position anteriorly displaces the upper and lower drive pegs 112, 113 in correspondence with anterior rotational displacement of the lower and upper ends 21, 22 of the upper and lower arms 12, 14, respectively.

Anterior displacement of the upper and lower drive pegs 112, 113 correspondingly anteriorly displaces the drive plate 109. Anterior displacement of the drive plate 109 correspondingly anteriorly displaces the upper and lower drive bushings 114, 115. Anterior displacement of the upper and lower drive bushings 114, 115 correspondingly rotationally displaces the lower and upper internal ends 133, 137 of the upper and lower tension strap levers 110, 111 and correspondingly posteriorly rotationally displaces the upper and lower external ends 132, 138 which have the connection points 154, 161 mounted thereon.

While the forgoing preferred embodiments of the invention have been described and shown, it is understood that alternatives and modifications, such as those suggested and others, may be made thereto and fall within the scope of the invention.

We claim:

1. An orthosis mountable on a knee having a patella to maintain proper tracking of the patella during movement of the knee, said orthosis comprising:
    an upper arm and a lower arm positionable about the knee;
    a hinge assembly positioned between said upper arm and said lower arm and positionable at the knee to one side of the patella, said hinge assembly having a hinge pivot and a tension strap lever including a tension strap connection point, wherein said upper arm, said lower arm and said tension strap lever are each rotatable about said hinge pivot to transition between a flexion position and an extension position;
    a tension strap connected to said tension strap lever at said tension strap connection point;
    a compression member positionable on the opposite side of the patella from said hinge assembly, said tension strap connected to said compression member to apply a tension force to said compression member, wherein said tension force increases when said tension strap lever rotationally transitions from said flexion position to said extension position and decreases when said tension strap lever rotationally transitions from said extension position to said flexion position; and
    means for applying a counter force to said compression member opposing said tension force.

2. The orthosis of claim 1 wherein said hinge assembly includes a lower end of said upper arm and an upper end of said lower arm and said hinge pivot includes an upper pivot element and a lower pivot element, wherein said lower end is rotatable about said upper pivot element, said upper end is rotatable about said lower pivot element and said tension strap lever is rotatable about said upper pivot element or said lower pivot element.

3. The orthosis of claim 1 wherein said hinge assembly further comprises a tension strap connector connecting said tension strap to said tension strap connection point of said tension strap lever.

4. The orthosis of claim 1 wherein said counter force applying means is a counterbalance connector connected to said compression member and oriented counter to said tension strap.

5. The orthosis of claim 1 wherein said compression member comprises a tracking guide engaging the knee and a compression plate in overlying engagement with said tracking guide.

6. The orthosis of claim 5 wherein said compression plate is formed from a more rigid material than said tracking guide and said tension strap is connected to said compression plate.

7. The orthosis of claim 1 wherein said compression member comprises a tracking guide engaging the knee.

8. The orthosis of claim 1 wherein said compression member comprises a compression plate.

9. The orthosis of claim 1 wherein said tension strap is an upper tension strap and said tension strap lever is an upper tension strap lever, said orthosis further comprising a lower tension strap and a lower tension strap lever including a lower tension strap connection point, wherein said lower tension strap lever is rotatable about said hinge pivot to transition between said flexion position and said extension position, and wherein said lower tension strap is connected to said lower tension strap at said lower tension strap connection point and is connected to said compression member.

10. The orthosis of claim 1 wherein said upper arm is a first upper arm, said lower arm is a first lower arm and said hinge assembly is a first hinge assembly, said orthosis further comprising a second upper arm and a second lower arm and a second hinge assembly positioned between said second upper arm and said second lower arm and positionable at the knee to the opposite side of the patella from said first hinge assembly.

11. The orthosis of claim 10 wherein said counter force applying means is a connector strap extending between said compression member and said second hinge assembly.

12. The orthosis of claim 1 further comprising a flexible tubular sleeve retaining said upper and lower arms.

13. The orthosis of claim 1 further comprising a stiffened upper cuff retaining said upper arm and a stiffened lower cuff retaining said lower arm.

14. An orthosis mountable on a knee having a patella to maintain proper tracking of the patella during movement of the knee, said orthosis comprising:
    an upper arm and a lower arm positionable about the knee;
    a hinge assembly positioned between said upper arm and said lower arm and positionable at the knee to one side of the patella, said hinge assembly having an upper pivot element, a lower pivot element, an upper tension strap lever including an upper tension strap connection point, and a lower tension strap lever including a lower tension strap connection point, wherein said upper arm and said upper tension strap lever are rotatable about said upper pivot element and said lower arm and said lower tension strap lever are rotatable about said lower pivot element to transition between a flexion position and an extension position;
    an upper tension strap connected to said upper tension strap lever at said upper tension strap connection point;
    a lower tension strap connected to said lower tension strap lever at said lower tension strap connection point;
    a compression member positionable on the opposite side of the patella from said hinge assembly, said upper and lower tension straps connected to said compression member to apply a tension force to said compression member, wherein said tension force increases when said upper and lower tension strap levers rotationally transition from said flexion position to said extension position and said tension force decreases when said upper and lower tension strap levers rotationally transition from said extension position to said flexion position; and
    means for applying a counter force to said compression member opposing said tension force.

15. The orthosis of claim 14 wherein said hinge assembly further comprises an upper tension strap connector connecting said upper tension strap to said upper tension strap connection point of said upper tension strap lever.

16. The orthosis of claim 14 wherein said hinge assembly further comprises a lower tension strap connector connecting said lower tension strap to said lower tension strap connection point of said lower tension strap lever.

17. The orthosis of claim 14 wherein said counter force applying means is a counterbalance connector connected to said compression member and oriented counter to said tension strap.

18. The orthosis of claim 14 wherein said compression member comprises a tracking guide engaging the knee.

19. The orthosis of claim 14 wherein said compression member comprises a compression plate.

20. The orthosis of claim 14 wherein said upper arm is a first upper arm, said lower arm is a first lower arm and said hinge assembly is a first hinge assembly, said orthosis further comprising a second upper arm and a second lower arm and a second hinge assembly positioned between said second upper arm and said second lower arm and positionable at the knee to the opposite side of the patella from said first hinge assembly.

21. The orthosis of claim 20 wherein said counter force applying means is a connector strap extending between said compression member and said second hinge assembly.

22. An orthosis mountable on a knee having a patella to maintain proper tracking of the patella during movement of the knee, said orthosis comprising:
- an upper arm and a lower arm positionable about the knee;
- a hinge assembly positioned between said upper arm and said lower arm and positionable at the knee to one side of the patella, said hinge assembly having a hinge pivot and a tension strap lever including a tension strap connection point, wherein said upper arm, said lower arm and said tension strap lever are each rotatable about said hinge pivot to transition between a flexion position and an extension position;
- a tension strap connected to said tension strap lever at said tension strap connection point;
- a compression member positionable on the opposite side of the patella from said hinge assembly, said tension strap connected to said compression member to apply a tension force to said compression member, wherein said tension strap connection point is posteriorly displaced more distal from the patella when said tension strap lever rotationally transitions from said flexion position to said extension position and said tension strap connection point is anteriorly displaced more proximal to the patella when said tension strap lever rotationally transitions from said extension position to said flexion position; and
- means for applying a counter force to said compression member opposing said tension force.

23. An orthosis mountable on a knee having a patella to maintain proper tracking of the patella during movement of the knee, said orthosis comprising:
- an upper arm and a lower arm positionable about the knee;
- a hinge assembly positioned between said upper arm and said lower arm and positionable at the knee to one side of the patella, said hinge assembly comprising,
  - a lower end of said upper arm,
  - an upper end of said lower arm,
  - an upper pivot element,
  - a lower pivot element,
  - an upper tension strap lever including an upper tension strap connection point,
  - a lower tension strap lever including a lower tension strap connection point, wherein said lower end of said upper arm and said upper tension strap lever are rotatable about said upper pivot element and said upper end of said lower arm and said lower tension strap lever are rotatable about said lower pivot element,
  - a drive plate,
  - an upper drive peg connecting said lower end of said upper arm with said drive plate,
  - a lower drive peg connecting said upper end of said lower arm with said drive plate,
  - an upper drive bushing connecting said drive plate with said upper tension strap lever, and
  - a lower drive bushing connecting said drive plate with said lower tension strap lever, wherein said upper and lower drive pegs displace said drive plate in response to rotation of said upper and lower arms in a first direction and said upper and lower drive bushings rotate said upper and lower tension strap levers in a second direction essentially opposite said first direction in response to displacement of said drive plate,
- an upper tension strap connected to said upper tension strap lever at said upper tension strap connection point;
- a lower tension strap connected to said lower tension strap lever at said lower tension strap connection point;
- a compression member positionable on the opposite side of the patella from said hinge assembly, said upper and lower tension straps connected to said compression member to apply a tension force to said compression member, wherein said tension force increases when said first direction is anterior and said second direction is posterior and said tension force decreases when said first direction is posterior and said second direction is anterior; and
- means for applying a counter force to said compression member opposing said tension force.

24. The orthosis of claim 23 wherein said drive plate is linearly anteriorly displaced when said first direction is anterior and is linearly posteriorly displaced when said first direction is posterior.

25. A method for maintaining proper patellar tracking during range of motion movement of a knee comprising:
- positioning a compression member to a first side of a patella of a knee, wherein said compression member is aligned with a desired dynamic patellar track;
- positioning a hinge assembly at said knee to a second side of said patella essentially opposite said first side, said hinge assembly providing rotation between an upper arm and a lower arm and said hinge assembly having a hinge pivot and a tension strap lever including a tension strap connection point, wherein said upper arm, said lower arm and said tension strap lever are each rotatable about said hinge pivot to transition between a flexion position and an extension position;
- connecting a tension strap to said compression member and said tension strap lever at said tension strap connection point;
- performing a range of motion movement on said knee by moving said knee from said flexion position to said extension position or from said extension position to said flexion position;
- posteriorly displacing said tension strap connection point away from said patella to tighten said tension strap and increase said tension force when said knee approaches said extension position; and anteriorly displacing said tension strap connection point toward said patella to slacken said tension strap and decrease said tension force when said knee approaches said flexion position.

* * * * *